US010945639B2

(12) United States Patent
Laan et al.

(10) Patent No.: US 10,945,639 B2
(45) Date of Patent: Mar. 16, 2021

(54) FITTING ROOM MIRROR

(71) Applicant: Van de Velde NV, Schellebelle (BE)

(72) Inventors: Dominicus Laan, Driebergen-Rijsenburg (BE); Lieve Vermeire, Zwijnaarde (BE); Geert Van Der Biest, Wanzele (BE); Michael Bal, Merelbeke (BE); Sabine Dotremont, Sint Amandsberg (BE); Roel De Rijck, Sint Amandsberg (BE); Tim Verbeeren, Denderhoutem (BE)

(73) Assignee: Van de Velde NV, Schellebelle (BE)

( * ) Notice: Subject to any disclaimer, the term of this patent is extended or adjusted under 35 U.S.C. 154(b) by 197 days.

(21) Appl. No.: 14/761,127

(22) PCT Filed: Jan. 14, 2014

(86) PCT No.: PCT/EP2014/050633
§ 371 (c)(1),
(2) Date: Jul. 15, 2015

(87) PCT Pub. No.: WO2014/111391
PCT Pub. Date: Jul. 24, 2014

(65) Prior Publication Data
US 2015/0359462 A1    Dec. 17, 2015

(30) Foreign Application Priority Data

Jan. 16, 2013 (EP) .................................. 13151448

(51) Int. Cl.
*H04N 7/15*    (2006.01)
*A61B 5/107*    (2006.01)
(Continued)

(52) U.S. Cl.
CPC ............ *A61B 5/1079* (2013.01); *A41H 1/02* (2013.01); *A61B 5/1072* (2013.01);
(Continued)

(58) Field of Classification Search
CPC .......... A41H 1/02; G02B 27/141; G06T 7/00; G06T 17/00; H04N 13/0239; H04N 7/144;
(Continued)

(56) References Cited

U.S. PATENT DOCUMENTS 5,339,198 A * 8/1994 Wheatly .................. G02B 1/04
359/359
5,530,652 A    6/1996 Croyle et al.
(Continued)

FOREIGN PATENT DOCUMENTS

EP    1 207 367 A1    5/2002
WO    2008/150343 A1    12/2008

OTHER PUBLICATIONS

International Search Report pertaining to Application No. PCT/EP2014/050633 with a filing date of Jan. 14, 2014.
(Continued)

*Primary Examiner* — Patrick E Demosky
(74) *Attorney, Agent, or Firm* — Dinsmore & Shohl LLP

(57) ABSTRACT

The present invention relates to a fitting room mirror including image capturing means and image processing means enabling the determination of body dimensions and in providing cloth-fitting advice to the user.

10 Claims, 3 Drawing Sheets

Voxel gridbox for capturing 3D scan

(51) Int. Cl.
*H04N 13/239* (2018.01)
*A41H 1/02* (2006.01)
*A61B 5/00* (2006.01)
*G06T 17/00* (2006.01)
*G01B 11/25* (2006.01)
*G02B 27/14* (2006.01)
*G06T 7/00* (2017.01)
*H04N 13/00* (2018.01)

(52) U.S. Cl.
CPC .......... *A61B 5/1077* (2013.01); *A61B 5/6888* (2013.01); *G01B 11/25* (2013.01); *G01B 11/2513* (2013.01); *G02B 27/141* (2013.01); *G06T 7/00* (2013.01); *G06T 17/00* (2013.01); *H04N 13/239* (2018.05); *A61B 5/0046* (2013.01); *A61B 2503/12* (2013.01); *G06T 2200/08* (2013.01); *G06T 2210/16* (2013.01); *H04N 2013/0081* (2013.01)

(58) Field of Classification Search
CPC ...... H04N 7/15; A61B 5/1079; A61B 5/1072; A61B 5/1077; G01B 11/25; G01B 11/2513
See application file for complete search history.

(56) References Cited

U.S. PATENT DOCUMENTS

| | | | | |
|---|---|---|---|---|
| 6,734,980 B1* | 5/2004 | Brash | ................... | G01B 11/245 356/601 |
| 2002/0126295 A1* | 9/2002 | Dudkiewicz | ......... | A61B 5/1077 356/601 |
| 2004/0196359 A1* | 10/2004 | Blackham | .............. | H04N 7/144 348/14.08 |
| 2004/0227752 A1 | 11/2004 | McCartha et al. | | |
| 2006/0116555 A1 | 6/2006 | Pavlidis et al. | | |
| 2008/0294012 A1* | 11/2008 | Kurtz | ................... | A61B 5/0059 600/300 |
| 2009/0040778 A1* | 2/2009 | Takayanagi | ............... | B60R 1/00 362/494 |
| 2009/0322745 A1* | 12/2009 | Zhang | ..................... | G06T 7/521 345/420 |
| 2010/0073461 A1 | 3/2010 | Hammes et al. | | |
| 2012/0196679 A1* | 8/2012 | Newcombe | .............. | A63F 13/06 463/36 |
| 2012/0253360 A1* | 10/2012 | White | ................ | A61B 19/5244 606/130 |
| 2012/0314729 A1 | 12/2012 | Ogawa et al. | | |
| 2013/0100240 A1* | 4/2013 | Liu | ........................ | H04N 7/144 348/14.08 |

OTHER PUBLICATIONS

Written Opinion pertaining to Application No. PCT/EP2014/050633 with a filing date of Jan. 14, 2014.
International Preliminary Report on Patentability pertaining to Application No. PCT/EP2014/050633 with a filing date of Jan. 14, 2014.
XP-002698385, Reflectivity—Wikipedia, http://en.wikipedia.org/wiki/Reflectvity, Jun. 13, 2013 09:30, pp. 1-4.

* cited by examiner

Voxel gridbox for capturing 3D scan

FITTING ROOM MIRROR

FIELD OF THE INVENTION

The present invention relates to a fitting room mirror including image capturing means and image processing means enabling the determination of body dimensions and in providing cloth-fitting advice to the user.

BACKGROUND TO THE INVENTION

There is a growing interest to the application of three-dimensional measurement of bodily dimensions in providing garment-fitting advice to people. At present such three-dimensional (3D) measurement is typically done using 3D-scanners such as the TC2 Scanner of Textile/Clothing Technology Corp., the scanner of Human Solutions GmbH and the automatic installation of Telmat Ind. SA as described in EP1207367. In the majority of said cases, the process of acquiring the 3D model includes the use of light, such as for example the use of structured light wherein a recognizable pattern of lines or pixels of lights is projected on the subject to be measured. Other methodologies employ laser triangulation, photogrammetry, and time-of-flight determinations. Recent developments in 3D-measurement techniques are the low cost body scanners, such as for example based on MS Kinect or comparable depth camera's, such as for example the TC2 KX16 scanner (see above), the styku-scanner or the scanner of Bodymetrics.

The existing techniques and environment for 3D scanning are very technically oriented and do not result in the perception that you expect to find in a fitting room, such as seclusion, curtain, mirror, lighting. Instead of a fitting room the user first enters a scan area within which the scanning equipment is installed. Said scan area is specifically adapted to the scan equipment, which results in a complete different experience to the user when compared to a standard fitting room. In order not to influence the measurements that are based on the use of light, ambient light is normally dimmed, thus exposing the user to flashes of light and/or light patterns of the laser beam used in the measurement. Further, to obtain a complete scan of the person cameras are either installed around, or move around the person to be measured. The scan result is subsequently used to give customized garment fitting advice, allowing the user to choose proper fitting clothes. The user's next step is to go from the scan area to the fitting room. The scan area and fitting room are clearly separated by a totally different experience. For many people this is a problem, both for consumers and for the shop owners:

the consumer prefers to go to the fitting room directly and wants to avoid the technical scan area, the shop owner needs extra space for the scan area and also prefers to help the consumer directly in the fitting room It would accordingly be desirable to have 3D scanning apparatus that could be seamlessly integrated in a standard garment fitting room without adaptations, i.e. without the need to change for example ambient light exposure and without the need to install visible scan equipment.

An effort to combine cameras with mirrors in 3D measurement devices is for example provided in PCT publication WO2008150343, also published as US2008/294012. In said reference the camera is positioned behind a semi-transparent mirror, or a flickering device that is driven electronically to switch between reflecting and transmitting states. However, a problem associated with this configuration is that it is necessary to find a compromise between the requisite of a good mirror image and sufficient transparency for the camera behind it.

Improving the mirror image will inevitably result in a worsening of the camera transparency and vice versa. For example a semi-transparent mirror with 50% reflection and 50% transmission will result in a mirror with a dark mirror image since 50% of the incident light is not reflected. Improving the mirror characteristics in increasing the reflection to 80% will improve the mirror image, but have a detrimental effect on the camera image, in particular when combined with structured light as part of the 3D scanning technique. In said instance only a fraction of the projected light is captured by the camera due to inevitable losses in the light transfer from the subject to the camera, with in particular the limited transparency (only 20%) of the mirror. In case the structured light is also projected from behind such a semi-transparent mirror the transparency of the mirror has an even bigger effect on the quality of the camera image as the light is passing the mirror twice. First in projecting the structured light onto the subject to be measured and second in capturing the reflected light with the camera. Using for example a mirror with a transparency of 20%, only up to (20% of 20%) 4% of the projected light may reach the camera. This is clearly insufficient.

It is accordingly an object of the present invention to address the aforementioned problems in 3D measuring devices and enable a 3D measuring device that can be seamlessly integrated in a garment fitting room as a fitting mirror, such that;

it can be used as a standard fitting mirror
it provides a good mirror image, i.e. bright with little or no change in colour (true colour)
it works under light conditions typically found in a fitting room
it does not generate undesired light effects like light flashes or laserbeams
it is capable to provide a complete 3D image of the user.

SUMMARY OF THE INVENTION

In a first aspect the present invention provides a three-dimensional measuring device for use in a garment fitting room comprising at least one image capturing means, a projector, and a wavelength specific mirror characterized in that said image capturing means is positioned behind said wavelength specific mirror, and in that said wavelength specific mirror is only efficient in transmitting electromagnetic waves with wavelengths in a range outside of the visible spectrum, and in the infrared spectrum. In other words, the wavelength specific mirror transmits such infrared waves for at least 70%. As evident from the examples provided in FIGS. 4 and 5, in a preferred embodiment the wavelength specific mirror transmits at least 90% of the wavelengths in the infrared spectrum, more in particular it transmits at least 70%, 75%, 80%, 85%, 90% or more of the wavelengths in the infrared spectrum; even more in particular wavelengths in the near infrared spectrum; in one embodiment wavelengths of at least 750 nm; more in particular near infrared light with wavelengths from about 800 nm to about 2500 nm. In one embodiment, both the image capturing means and the projector are positioned behind said wavelength specific mirror.

As detailed further hereinafter, in a particular embodiment of the present invention the wavelength specific mirror used in the three-dimensional measuring device according to the present invention reflects all the visible light wavelengths. In other words it reflects electromagnetic waves with wavelengths in the visible spectrum (from about 380 nm to about 740 nm) and is transparent for electromagnetic waves with wavelengths outside of said spectrum and within the infrared spectrum.

In reflecting the visible light wavelengths, said wavelengths may be fully reflected, but in an alternative embodiment and in particular when combined with further displaying means, the mirror reflects the visible light wavelengths for at least 70%, 75%, 80%, 85%, 90% or more.

In the present invention the wavelength specific mirror is efficient in transmitting infrared light, namely infrared light with wavelengths of at least 750 nm; more in particular near infrared light with wavelengths from about 800 nm to about 2500 nm.

In the three-dimensional measuring method the projector preferably projects structured electromagnetic waves on the three-dimensional object to be measured. In said process a known pattern is projected, typically consisting of a grid or a set of parallel stripes, on the three-dimensional object to be measured. By determining the way this pattern deforms on the surface of said object, an exact geometric reconstruction of the surface can be calculated.

Where the optical resolution of this measurement technique is to an important extend determined by the width of the stripes used and their optical quality, further improvement can be realized by capturing a plurality of images with a slightly shifted pattern. Thus in a particular embodiment the measuring method as provided, is further characterized in that at least 3 exposures are taken with slightly shifted pattern. Shifting of the pattern may be realized by moving the image capturing means and/or the projector, alternatively by moving the object to be measured. In a particular embodiment capturing of the images is accordingly realized using a high-frame-rate structured light camera(s).

Instead of moving the projector and/or image capturing means behind the wavelength specific mirror, capturing of slightly shifted patterns could also be realized by using a plurality of image capturing means and/or projectors. Within a particular embodiment of the present invention the three-dimensional measuring device comprises two or more image capturing means, in particular two image capturing means. In another embodiment the three-dimensional measuring device comprises two or more projectors; in particular two projectors. In a more particular embodiment of the present invention the three-dimensional measuring device comprises two or more image capturing means, and two or more projectors; even more in particular two image capturing means, and two projectors.

In as far there is no particular limitation regarding the mutual orientation of said two or more image capturing means and/or projectors; in a preferred embodiment said image capturing means and/or projectors are oriented along the same vertical axis.

As already mentioned hereinbefore, and in particular when the wavelength specific mirror only partially reflects the visible wavelengths, the three-dimensional measuring device according to present invention, may further comprise display means positioned behind said wavelength specific mirror. This display could for example be used to display garment fitting information or user instructions to the subject using the three-dimensional measuring device according to the present invention.

In a further aspect the present invention provides the use of the three-dimensional measuring device(s) as described herein, as mirror; in particular as mirror in a garment fitting room.

It is also an object of the present invention to provide a method for the acquisition of three-dimensional shapes of an object, in particular human subjects; more in particular garment sizes of said subject, said method comprising; placing the three dimensional object to be measured in front of a wavelength specific mirror as defined herein; projecting structured electromagnetic waves, in particular infrared light, on said object from a projector positioned behind said wavelength specific mirror; capturing images from the structured waves, in particular from the structured infrared light, projected on the object using image capturing means positioned behind said wavelength specific mirror; transmit said captured images from said image capturing device to a computer processor and have said computer processor process said image to determine the three-dimensional shape of said object.

Further to the above, one method to shift the pattern on the object to be measured is by moving said object, accordingly in a further embodiment the measuring method includes the step of rotating the object or causing said object to rotate in front of the wavelength specific mirror.

In a further embodiment of the method according to the invention, the images are captured at high frame rates.

In another embodiment of the method according to the invention, the projector projects structured near infrared light on the object to be measured.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
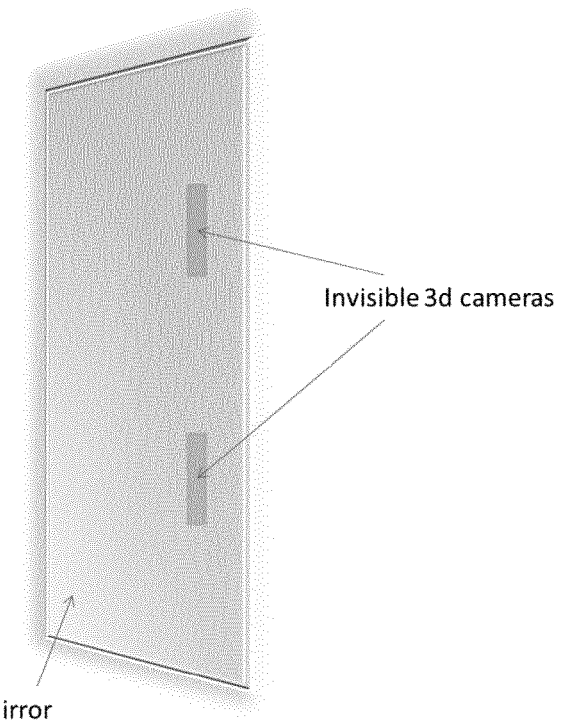
FIG. 1: Schematic drawing of the 3D measuring device according to the present invention, showing the mirror and the position of the 3D cameras behind the mirror. Within this presentation the number of cameras and position are only given as an example. Actual number and position will depend among others on scan technology, scan task, and size of mirror.
Figure 2:
FIG. 2: Schematic drawing showing the step of moving the subject in front of the mirror in the measuring method. In the exemplified embodiment the user is requested to rotate in front of the mirror, preferably whilst raising his arms.

The invention as described herein addresses the problems associated with the present 3D measuring devices, in particular when for use in garment fitting room. As already detailed hereinbefore, the 3D measuring device of the present invention presents itself as a mirror, with hidden integration of the 3D cameras and processing means. As schematically represented in FIG. 1, the camera(s) and processing means are positioned behind a wavelength specific mirror. In a particular embodiment along a vertical axis over the length of said mirror. This mirror can simply be placed as a standard mirror in a fitting room. Thus different from the prior art scanning devices, there is no longer a separate scanning room, but the user can directly go to the fitting room and only sees a mirror with a high quality mirror image, as he/she would expect. To make the 3D scan available, the user only needs to turn around in front of the mirror (see FIG. 2). Again no particular adaptations of the environmental conditions are required; there is no need to change (dim) the lightning in the fitting room and the user will experience no annoying flashing lights or lasers. The scan can then be used for example for providing cloth-fitting advice or for other purposes.

To achieve the foregoing and as reflected in the wording of the different embodiments of the present invention, the measuring device combines the following features. It makes use of wavelengths outside the visible spectrum, in particular wavelengths within the infrared spectrum, and it makes use of a wavelength specific mirror that is only efficient in transmitting electromagnetic waves with wavelengths in a range outside of the visible spectrum and within the infrared spectrum.

In the 3D measuring method it preferably uses structured electromagnetic waves with wavelengths outside of the visual spectrum; more in particular structured infrared wavelengths. Further optimization in the 3D measuring method resides in the image sampling frequency, consequently preferably high frame rate cameras are used. As already explained herein above, when using structured light the projectors project a pattern on the object to be measured. Deformation of the pattern by said object is captured by the camera (image capturing device) and can be used to determine geometry of said object. As used herein, structured waves are chosen outside the visible spectrum, and in particular consist of near infrared waves. As such, there is no visual experience to the user, rendering the method less intrusive when compared to the use of structured visible light.

Irrespective of the chosen wavelength, the use of structured waves results in a stable and fast method of rendering a complete and detailed 3D model of the object being measured, in particular when used with high frame rate cameras. As already explained above, quality of the 3D image improves in case images are taken with slightly shifted patterns. This may be achieved by moving the cameras, but again and in order to minimize measuring perception to the user, in the methods of the present invention the cameras are preferably kept stationary during the actual measurement. In said instance, shifting of the pattern can only be realized by moving the object (rotation in front of the mirror) instead. In order to have sufficient detail, and images that are only slightly shifted in pattern, it is in said embodiment accordingly desirable to use high frame rate cameras as mentioned above. A typical example of a high frame rate camera that can be used in the methods of the present invention, is the Microsoft® Kinect using a near infrared light pattern.

Figure 3:
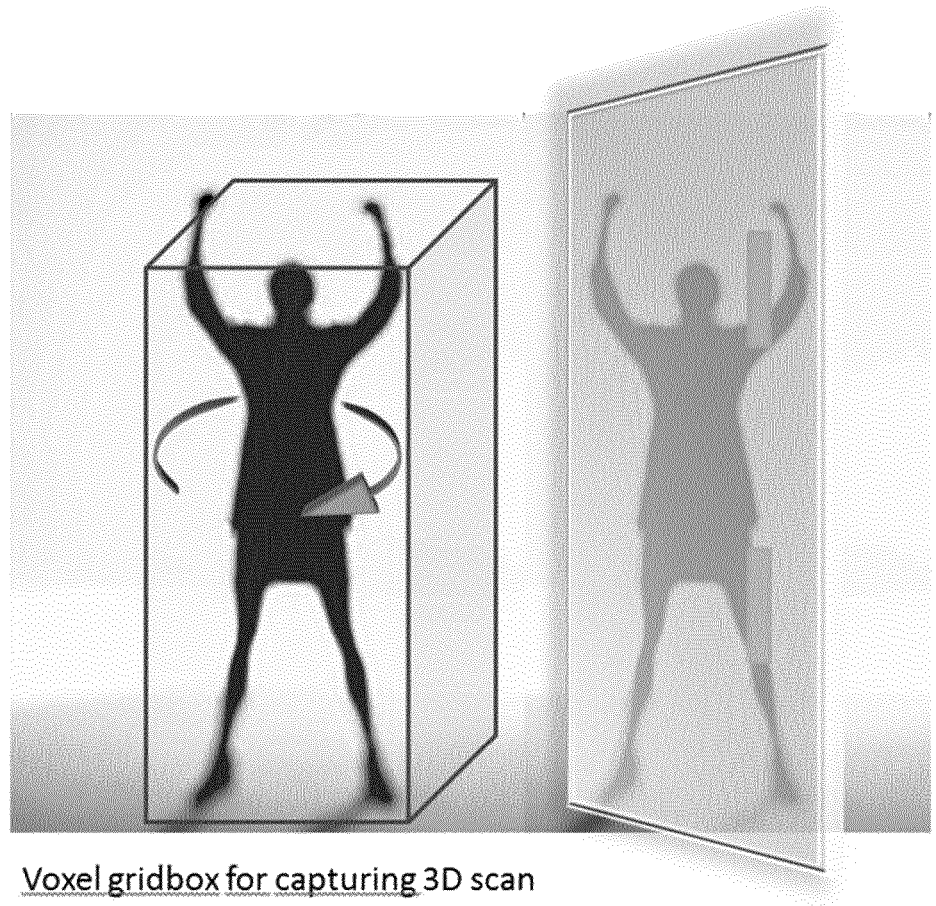
FIG. 3: Schematic drawing showing a further step in the processing of the captured images, in the 3D measuring method according to the present invention. The captured images are combined into a 3D image in a voxel grid volume surrounding the user.

Thus in one particular embodiment of the present invention, the person is requested to make a full 360° rotation in front of the mirror in a comfortable rate of about 4 seconds. During this movement a pattern of structured waves outside the visual spectrum are projected on said person and images (preferably using stationary cameras) are captured at a frame rate of at least 10 frames per second, preferably 20 frames per second, more preferably at least 25 frames per second; even more preferably at least 30 frames per second or more. The thus obtained images are processed in a virtual voxel gridbox surrounding said person (see FIG. 3) and combined to yield a complete 3D scan of the person in front of the mirror. Throughout this process the camera(s) are positioned out of sight to the user in that they are positioned behind the wavelength specific mirror. Where the cameras are stationary during the measurement, just prior to the measurement their position may be adjusted to the bodily dimensions of the person using the measuring mirror. In other words, the position of the image capturing device(s) behind the mirror is adjustable.

Figure 4:
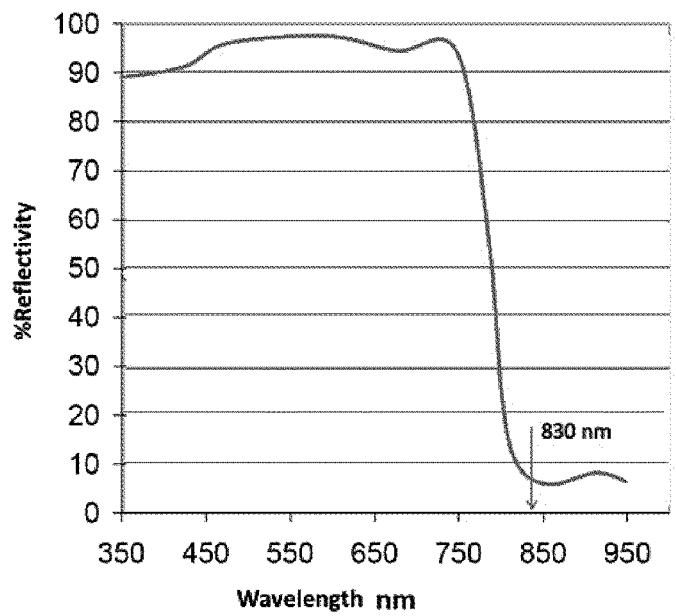
FIG. 4: Representative wavelength reflection diagram for a wavelength specific mirror to be used in the present invention. As evident from this scheme, this mirror quasi fully reflects visual light wavelengths.
Figure 5:
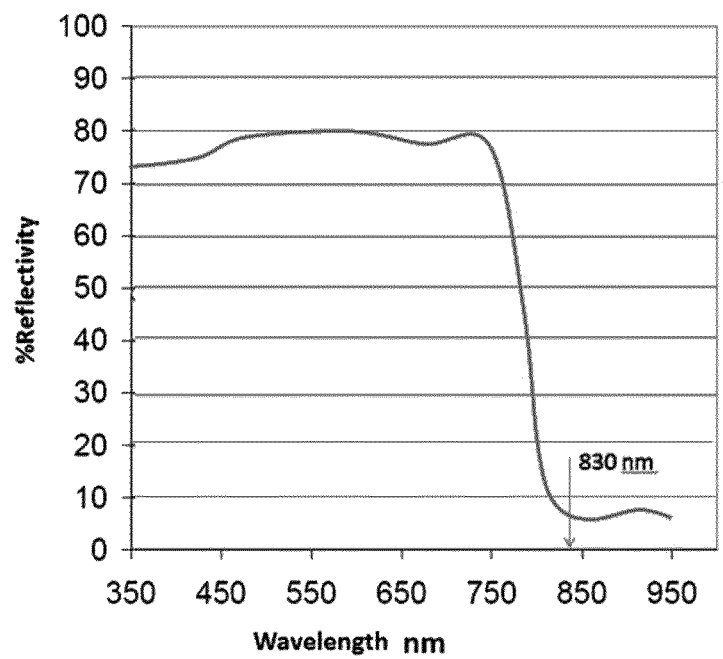
FIG. 5: Representative wavelength reflection diagram for a wavelength specific mirror to be used in the present invention. This mirror is partially transparent for visual light in that it reflects about 80% of the visual light wavelengths.

In a particular embodiment of the present invention the projector is also positioned behind the wavelength specific mirror. In either instance, the mirror is characterized in that it is only efficient in transmitting electromagnetic waves within the infrared spectrum. In other words, the mirror reflects visible lights, i.e. for at least 70%. As such, to the eyes of a human, the measuring mirror behaves as a standard mirror with a bright mirror image with no or only little change in colour. Such wavelength specific mirrors could be obtained using particular coatings, such as for example provided by Thin Metal Films Ltd from the UK. Dependent on the non-visible wavelengths chosen to be detected by the image capturing device a given coating will be required. For example, when using near infrared light a cold mirror with a wavelength reflection diagram comparable to FIG. 4 could be used. In case the measuring mirror is further combined with an information display positioned behind the mirror the latter should have a limited transparency for visible light. Thus in one embodiment the mirror may be chosen to be not nearly 100% reflective to the visible spectrum (see FIG. 4), but for example, 80% (FIG. 5). The mirror looks still bright and colourfast. The limited permeability to visible light can be used to put an information display behind the mirror. The limited (20%) visible light transmittance can be compensated in using a display with a high degree of brightness.

The invention claimed is:

1. A three-dimensional measuring device for use in a garment fitting room comprising at least one image capturing means, a projector, and a wavelength specific mirror, wherein said image capturing means is positioned behind said wavelength specific mirror, wherein said wavelength specific mirror transmits at least 70% of infrared light with wavelengths of at least 750 nm and reflects at least 85% of visible light wavelengths from 380 nm to 740 nm, wherein said projector is positioned behind said wavelength specific mirror, and wherein the projector projects structured infrared light through said wavelength specific mirror and onto the three-dimensional object to be measured such that the structured infrared light waves are reflected off the three-dimensional object to be measured and captured by said image capturing means that is positioned behind the wavelength specific mirror, the structured infrared light consisting of wavelengths in a range outside of the visual spectrum, and wherein the capturing means consists of one or more structured light camera having a frame rate of at least 10 frames per second.

2. The three-dimensional measuring device according to claim 1, further comprising display means positioned behind said wavelength specific mirror.

3. The three-dimensional measuring device according to claim 1, comprising two or more image capturing means.

4. The three-dimensional measuring device according to claim 3, wherein said image capturing means are oriented along the same vertical axis.

5. The three-dimensional measuring device according to claim 1, comprising two or more projectors.

6. The three-dimensional measuring device according to claim 5, wherein said two or more projectors are positioned behind the wavelength specific mirror.

7. The three-dimensional measuring device according to claim 6, wherein said two or more projectors are oriented along the same vertical axis.

8. A method for the acquisition of three-dimensional shapes of an object, said method comprising:

placing the three dimensional object to be measured in front of a wavelength specific mirror as defined in claim 1;

projecting from a projector positioned behind the wavelength specific mirror structured near infrared light consisting of wavelengths in a range outside of the visual spectrum through said wavelength specific mirror on said object;

capturing images from the structured near infrared light waves projected on the object using image capturing means positioned behind said wavelength specific mirror;

transmitting said captured images from said image capturing device to a computer processor and having said computer processor process said image to determine the three-dimensional shape of said object.

9. The method according to claim 8, further including rotating the object or causing said object to rotate in front of the wavelength specific mirror.

10. The method according to claim 8, wherein the images are captured at a frame rate of at least 10 frames per second.

* * * * *